United States Patent
Giuliani et al.

(10) Patent No.: US 10,550,094 B2
(45) Date of Patent: Feb. 4, 2020

(54) COMPOUNDS HAVING ANTIOXIDANT ACTIVITY AGAINST FREE RADICALS AND ANTI-INFLAMMATORY ACTIVITY, AND CORRESPONDING PHARMACEUTICAL OR COSMETIC COMPOSITIONS FOR SKIN CARE

(71) Applicant: GIULIANI S.P.A., Milan (IT)

(72) Inventors: Giammaria Giuliani, Montagnola (CH); Anna Benedusi, Milan (IT); Barbara Marzani, Carbonara Al Ticino (IT); Sergio Baroni, Villa d'Adda (IT)

(73) Assignee: Giuliana S.P.A., Milan (IT)

( * ) Notice: Subject to any disclaimer, the term of this patent is extended or adjusted under 35 U.S.C. 154(b) by 0 days.

(21) Appl. No.: 15/561,611

(22) PCT Filed: Mar. 23, 2016

(86) PCT No.: PCT/EP2016/056365
§ 371 (c)(1),
(2) Date: Sep. 26, 2017

(87) PCT Pub. No.: WO2016/151009
PCT Pub. Date: Sep. 29, 2016

(65) Prior Publication Data
US 2018/0072698 A1 Mar. 15, 2018

(30) Foreign Application Priority Data
Mar. 26, 2015 (IT) .................. 102015000009906

(51) Int. Cl.
C07D 319/06 (2006.01)
C07D 407/04 (2006.01)
A61Q 17/00 (2006.01)
A61K 8/49 (2006.01)

(52) U.S. Cl.
CPC ............ *C07D 319/06* (2013.01); *A61K 8/498* (2013.01); *A61Q 17/00* (2013.01); *C07D 407/04* (2013.01)

(58) Field of Classification Search
CPC .... C07D 319/06; C07D 407/04; A61K 8/498; A61Q 17/00
See application file for complete search history.

(56) References Cited

U.S. PATENT DOCUMENTS 2,853,495 A * 9/1958 Ruskin .................. C07C 255/00
536/1.11
3,987,189 A 10/1976 Hans et al.

FOREIGN PATENT DOCUMENTS

DE 2526312 A1 12/1976
EP 0345362 A1 12/1989
WO 2006/017726 A2 2/2006

OTHER PUBLICATIONS

Angyal & Lawler, 66 J. Am. Chem. Soc. 837-8 (1944) (CAS Abstr.) (Year: 1944).*
International Search Report and Written Opinion for corresponding Application No. PCT/EP2016/056365 (dated May 23, 2016).
International Preliminary Report on Patentability for corresponding Application No. PCT/EP2016/056365 (dated May 22, 2017).
Wardrop et al., "Template-Directed C—H Insertion: Synthesis of the Dioxabicyclo[3.2.1]octane Core of the Zaragozic Acids," Org. Letts. 3(15):2261-2264 (2001).
Bonner et al., "Furfurylidene Derivatives of Glucitol," J. Chem. Soc. C:2229-2233 (1966).
Emmi et al., "The Selective OH Radical Oxidation of Sorbitylfurfural: A Combined Experimental and Theoretical Study," J. Phys. Chem. 106(18):4598-4607 (2002).
Bourne et al., "Studies of Trifluoroacetic Acid. Part XVII. Reaction of Acyl Trifluoroacetates with [Beta]C-, [Beta]-, and [Alpha]Acetals of D-Glucitol," J. Chem. Soc. 1959:1864-1870 (1959).
Hann et al., "The 3,5-Benzylidene and 3,5-Methylene Acetals of Gluco-Gulo-Hepitol," J. Am. Chem. Soc. , 68:1769-1774 (1946).
Zanoli et al., "Influence of 2,4-Tetra-O-Methyl-Furfurylidene-Sorbitol (MSF) on Carrageenan-Induced Inflammation and Anti-Inflammatory and Toxic Effects of Indomethacin in Rats," Agents and Actions 12(4):521-526 (1982).

* cited by examiner

*Primary Examiner* — Timothy R Rozof
(74) *Attorney, Agent, or Firm* — Pepper Hamilton LLP

(57) ABSTRACT

The invention relates to compounds having general formula (I): where R=H, $CH_2$—OH, $CH_2$—O—CO—$CH_3$, $CH_2$—O—CO-Ph (Ph=phenyl) R'=H, $CH_2$—O—CO—$CH_3$, $CH_2$—O—CO-Ph (Ph=phenyl) Ar=phenyl, 3-methoxy-4-hydroxy phenyl, 2-furyl. These are compounds having antioxidant activity against free radicals together with anti-inflammatory activity, the compounds being useful as active ingredients for the preparation of pharmaceutical dermatological or cosmetic compositions for skin care.

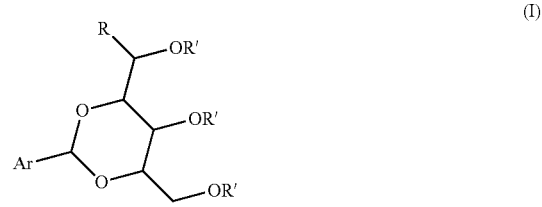

(I)

6 Claims, No Drawings

COMPOUNDS HAVING ANTIOXIDANT ACTIVITY AGAINST FREE RADICALS AND ANTI-INFLAMMATORY ACTIVITY, AND CORRESPONDING PHARMACEUTICAL OR COSMETIC COMPOSITIONS FOR SKIN CARE

This application is a national stage application under 35 U.S.C. § 371 of PCT Application No. PCT/EP2016/056365, filed 23 Mar. 2016, which claims priority of Italy Application No. 102015000009906, filed 26 Mar. 2015, which are hereby incorporated by reference in their entirety.

FIELD OF THE INVENTION

The present invention relates to compounds having antioxidant activity against free radicals together with anti-inflammatory activity, these compounds being useful as active ingredients for the preparation of pharmaceutical dermatological or cosmetic compositions for skin care.

BACKGROUND OF THE INVENTION

The primary function of the skin is to form a physical and chemical barrier between the external environment and the internal environment of the body, protecting the latter from harmful stimuli such as trauma, pathogenic agents or irritants, often through an inflammatory response. In fact, since inflammation helps to eliminate damaged cells so as to avoid further tissue damage, it is considered a protection mechanism against pathogenic organisms and other harmful agents.

The strength and duration of the inflammatory response depends on the context and type of stimulus; usually, the early stages of the inflammatory response form part of the so-called innate immune response.

In the skin, the production of ROS (Reactive Oxygen Species) free radicals at the skin level is a physiological mechanism which forms part of the normal cell metabolism, such as mitochondrial respiration. Moreover, the ROS free radicals can form after exposure to environmental stimuli and subsequent reactions of the immune system. ROS are normally neutralized by both enzymatic and non-enzymatic antioxidants, thereby keeping a balance between oxidant/antioxidant with tissue homeostasis.

However, excessive levels of ROS due to either a high production under stimulus or to an insufficient antioxidant activity lead to the so-called oxidative stress, with harmful effects through oxidative modification and functional and structural damage to biomolecules, such as lipids, proteins and DNA; or through dysregulation of cell signaling pathways, with triggering of downstream signaling cascades leading to the impaired release of cytokines, resulting in an exacerbation of inflammation.

Oxidative stress is a physiological condition in which there is an imbalance between the concentrations of reactive oxygen species (ROS) and antioxidants. An excessive accumulation of ROS leads, as said, to cellular damage, which can result in the development of many serious diseases: cancer, diabetes, cardiovascular diseases, atherosclerosis and neurodegenerative diseases. Under normal physiological conditions, the generation of cell ROS is counterbalanced by the action of cellular antioxidant enzymes and other redox molecules. Because of their potential harmful effects, excess ROS must be promptly eliminated from cells through antioxidant defense mechanisms. Compounds with antioxidant properties are therefore both hydrophilic and lipophilic molecules capable of metabolizing and eliminating the ROS.

In most cases, skin inflammation may initially be considered a protective process which develops to limit the damage from an injury or infection. However, the skin may also be subjected to excessive inflammatory responses resulting in the onset of chronic inflammation, auto-inflammation and autoimmunity. Acute inflammation of the skin can develop after the exposure to high doses of UV radiation (for example, sunburns), contact with allergens or chemical irritants. However, chronic inflammation of the skin is the result of a too sustained inflammatory response which ultimately seriously influences the skin health.

For example, in allergic contact dermatitis the relationship between ROS and inflammatory process was described by Esser et al., Contact Sensitizers Induces Skin Inflammation via ROS Production and Hyaluronic Acid Degradation, www.plosone.org, Volume 7|Issue 7|e41340, 2012. The data obtained identify an indirect mechanism of sensitization which induces the innate inflammatory response involving the degradation of the extracellular matrix ECM due to hyaluronic acid degradation by the ROS.

It is also known that skin inflammation leads to an alteration of the basic function of the skin barrier which, through a vicious circle, exacerbates the inflammatory condition itself and the ROS production. A defective cutaneous barrier permeability allows environmental allergens to penetrate the skin, resulting in the onset of immunological responses and of the inflammatory process.

In particular, the alteration of the barrier function is a central event in various skin alterations and diseases, such as sensitive skin, allergies (allergic and irritative dermatitis), eczema forms, atopic dermatitis, psoriasis.

Recent studies have shown that both environmental factors, such as UV radiation, and psychological stress are factors which can disrupt homeostasis and skin permeability.

In particular, published studies, such as Altemus et al., Stress-Induced Changes in Skin Barrier Function in Healthy Women, The Journal of Investigative Dermatology, Vol. 117, no. 2, 2001, or Denda et al., Stress alters cutaneous permeability barrier homeostasis, American Journal of Physiology, Vol. 278 no. 2, 2000, support the concept that psychological stress plays a determinant role in both the onset and in the severity of skin diseases such as psoriasis and atopic dermatitis.

EP0345362, owned by the same Applicant, describes active compounds, namely 2,4-monofurfurilidene-sorbitol and the relative tetra-ether 2,4-monofurfurilidene-1,3,5,6-O-tetra-alkyl-sorbitol, having an action of preventing the formation of endogenous and exogenous free radicals, and for this reason useful in cosmetic compositions for counteracting premature skin aging due to the action of the free radicals themselves. However, no anti-inflammatory activity is described for such compounds, nor are experimental data, which may be related to the skin barrier function or which may demonstrate other activities, reported.

It is the object of the present invention to propose compounds having antioxidant activity against ROS together with an anti-inflammatory activity, in particular capable of maintaining and restoring the barrier function of the skin, when compromised, suitable for pharmaceutical dermatological use or for cosmetic use for skin health and care.

SUMMARY OF THE INVENTION

According to the present invention, it has now been found that such combined actions are effectively obtained by using polyol derivatives as active compounds in pharmaceutical or cosmetic compositions, having general formula (I):

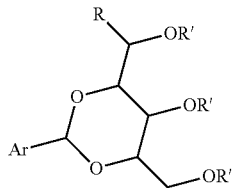
(I)

where R=H, CH$_2$—OH, CH$_2$—O—CO—CH$_3$, CH$_2$—O—CO-Ph (Ph=phenyl)

R'=H, CH$_2$—O—CO—CH$_3$, CH$_2$—O—CO-Ph (Ph=phenyl)

Ar=phenyl, 3-methoxy-4-hydroxy phenyl, 2-furyl.

Preferred compounds of formula (I) according to the invention are as follows:

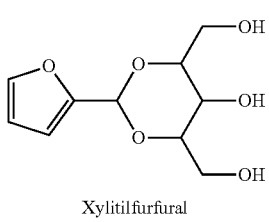
Xylitilfurfural

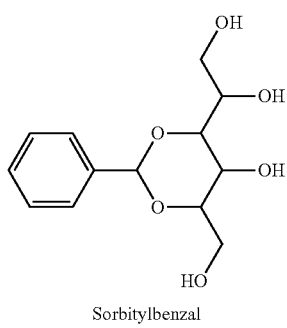
Sorbitylbenzal

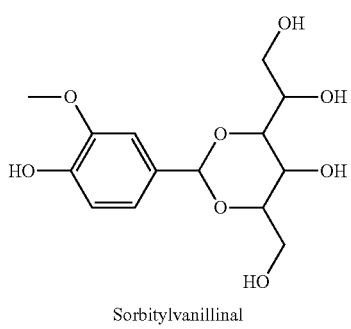
Sorbitylvanillinal

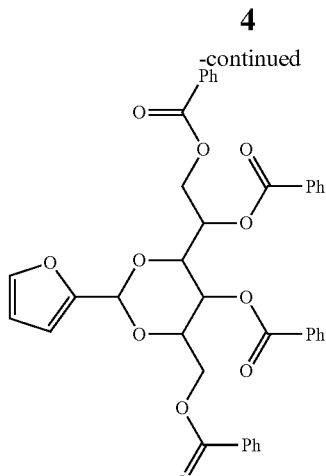
Tetrabenzoyl sorbitylfurfural

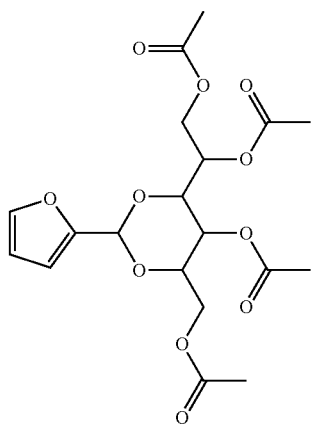
Tetraacetyl sorbitylfurfural

The invention also relates to dermatological pharmaceutical or cosmetic compositions for skin care, scalp included, which comprise one or more of said compounds of formula (I) as active ingredient capable of carrying out an antioxidant activity against free radicals together with an anti-inflammatory activity, in particular also capable of maintaining and restoring the barrier function of the skin, when compromised.

A composition of the invention is preferably formulated for topical administration on the skin or scalp, and comprises said active ingredient in an amount preferably in the range from 0.001 to 2.0% w/w with respect to the weight of the composition.

DETAILED DESCRIPTION OF THE INVENTION

The following are non-limiting examples of compositions of the invention suitable for pharmaceutical dermatological use or for cosmetic use for the skin health and care.

The amounts of the components, identified by the INCI nomenclature, are expressed as a percentages by weight variable within the ranges described.

Example 1

Serum to Counteract Skin Aging

| Ingredient | Qty (% w/w) |
| --- | --- |
| Red vine glycolic extract | 1-4 |
| Methyl gluceth-20 | 1-4 |
| Sepiplus S | 0.6-2.4 |
| Euxyl PE9010 | 0.6-2.2 |
| Glycerin | 0.5-2 |
| Oleth-20 | 0.5-2 |
| Caprylyl glycol | 0.3-1.2 |
| Natrlquest E 30 | 0.2-0.7 |
| Oxynex ST Liquid | 0.15-0.61 |
| Parfum | 0.13-0.51 |
| Ammonium acryloyldimethyltaurate/VP copolymer | 0.08-0.3 |
| Borage seeds extract | 0.05-0.2 |
| Sorbityl vanillinal | 0.05-0.2 |
| Catechin | 0.015-0.061 |
| Sodium hyaluronate | 0.01-0.04 |
| Tocotrienol | 0.01-0.04 |
| Dimethylmethoxy chromanol | 0.0005-0.002 |
| Quercetin | 0.0005-0.002 |
| Rutine | 0.0005-0.002 |
| Fermented soy | 0.0005-0.002 |
| Aqua | as needed to 100 |

Example 2

Anti-aging Anti-spot Facial Cream SPF50

| Ingredient | Qty (% w/w) |
| --- | --- |
| Ethylhexyl methoxycinnamate | 5-10 |
| Diethylamino Hydroxybenzoyl Hexyl Benzoate | 5-10 |
| C12-15 Alkyl benzoate | 4-16 |
| Di-n-butyl adipate | 4-14 |
| Ethylhexyl salicylate | 3-5 |
| Octocrylene | 3-10 |
| Titanium dioxide (silica coated) | 2-8 |
| Abil care XL 80 | 2-7 |
| Bis-Ethylhexyloxyphenol Methoxyphenyl Triazine | 1-4.1 |
| Diethylhexyl butamido triazone | 1-4.1 |
| Propylene glycol | 0.6-2.4 |
| Steareth-21 | 0.6-2.4 |
| Silica | 0.5-2 |
| Phenoxyethanol | 0.3-1 |
| Symdiol 68 | 0.3-1 |
| Ammonium acryloyldimethyltaurate/VP copolymer | 0.15-0.61 |
| *Calendula* oily extract | 0.1-0.41 |
| Lactic acid sol. 80% | 0.08-0.3 |
| Beta-glycyrrhetic acid 18 | 0.05-0.2 |
| Disodium EDTA dihydrate | 0.03-0.1 |
| Oxynex ST Liquid | 0.03-0.1 |
| Fermented soy | 0.03-0.1 |
| Vitamin E acetate | 0.03-0.1 |
| Sorbityl vanillinal | 0.02-0.08 |
| Sodium hydroxide | 0.011-0.045 |
| Ferulic acid | 0.005-0.02 |
| Aqua | as needed to 100 |

Example 3

Anti-aging Anti-wrinkle Cream

| Ingredient | Qty (% w/w) |
| --- | --- |
| C30-45 Alkyl cetearyl dimethicone crosspolymer | 0.7-3.6 |
| Cyclopentasiloxane | 10-35 |
| Polysilicone-11 | 2-8 |
| 1,3-Butylene glycol | 1.5-5.8 |
| HDI/trimethylol hexyllactone crosspolymer | 1.0-5.8 |
| Polyoxyethylene (2) stearyl ether | 0.7-2.9 |
| Ammonium acryloyldimethyltaurate/VP copolymer | 0.5-2.1 |
| Stearic acid | 0.5-1.9 |
| Glycerin | 0.5-1.9 |
| Inositol | 0.5-1.9 |
| Steareth-21 | 0.5-1.9 |
| Phenoxyethanol | 0.4-1 |
| Polymethyl methacrylate | 0.4-1.7 |
| Dicaprylyl carbonate | 0.4-1.6 |
| Caprylyl glycol | 0.3-1.2 |
| Borage seeds extract | 0.2-1 |
| Parfum | 0.2-0.7 |
| Dimethicone | 0.5-5.0 |
| Silica | 0.05-1.0 |
| Diazolidinyl Urea | 0.12-0.49 |
| Avocadol | 0.1-0.39 |
| Betaine | 0.05-0.19 |
| Sorbityl benzal | 0.05-0.19 |
| Panthenol | 0.05-0.19 |
| Xantan gum | 0.04-0.17 |
| Dissolvine GL47-S | 0.04-0.16 |
| Pentaerythrityl tetra-di-t-butyl hydroxyhydrocinnamate | 0.02-0.1 |
| Sodium hyaluronate | 0.02-0.1 |
| Tocotrienol | 0.01-0.039 |
| Dimethylmethoxy chromanol | 0.005-0.019 |
| Rutine | 0.0002-0.001 |
| Aqua | as needed to 100 |

Example 4

BB (Blemish Balm) Cream

| Ingredient | Qty (% w/w) |
| --- | --- |
| Octocrylene | 3-12 |
| CI 77891 | 3-10 |
| Ethylhexyl salicylate | 3-5 |
| Isododecane | 2-9 |
| Cetearyl alcohol | 2-8 |
| Glycerin | 2-8 |
| C12-13 Alkyl lactate | 1.5-6 |
| Butyl methoxydibenzoylmethane | 1.3-5 |
| Polymethylsilsesquioxane | 1.3-5 |
| Glyceryl stearate | 0.8-3 |
| Phenoxyethanol | 0.5-1 |
| Ethylhexylglycerin | 0.5-1.9 |
| Diethylhexyl syringylidenemalonate | 0.5-1.9 |
| CI 77492 | 0.5-1.8 |
| Benzyl alcohol | 0.4-1 |
| Cetereth-4 | 0.3-1 |
| Sodium cetearyl sulfate | 0.3-1 |
| CI 77491 | 0.15-0.6 |
| Sodium dehydroacetate | 0.15-0.4 |
| Xanthan gum | 0.15-0.6 |
| CI 77499 | 0.1-0.4 |
| Galactoarabinan | 0.1-0.4 |
| Caprylic/capric triglyceride | 0.05-0.2 |
| Dehydroacetic acid | 0.05-0.2 |
| *Physalis angulata* extract | 0.013-0.051 |
| Sodium hyaluronate | 0.01-0.04 |
| Tocopherol | 0.0001-0.0004 |
| Sorbityl furfural tetraacetate | 0.005-0.021 |
| Aqua | as needed to 100 |

Example 5

Night Cream to Counteract Skin Aging

| Ingredient | Qty (% w/w) |
|---|---|
| Protelan ENS | 2-10 |
| Fancol VB | 2-8 |
| Butylene glycol dicaprylate/dicaprate | 1.5-5.9 |
| Butylene glycol cocoate | 0.5-2.7 |
| C12-15 Alkyl benzoate | 1.5-5.9 |
| Dimethicone | 1.5-5.9 |
| Isostearyl alcohol | 0.5-2.5 |
| Optiphen | 0.7-3 |
| Aquaxyl | 0.5-2 |
| Betaine | 0.5-2 |
| Cetearyl alcohol | 0.5-2 |
| Ethylcellulose | 0.05-0.15 |
| Cetyl alcohol | 0.5-2 |
| Glycerin | 0.5-2 |
| Ammonium acryloyldimethyltaurate/VP copolymer | 0.2-1 |
| White lupin seeds extract | 0.2-1 |
| Gatuline expression | 0.2-1 |
| *Olea europaea* oil unsaponifiables | 0.2-1 |
| Trehalose dihydrate | 0.2-1 |
| Vitamin E acetate | 0.2-1 |
| Acrylates/C10-30 alkyl acrylate crosspolymer | 0.15-0.59 |
| Parfum | 0.1-0.4 |
| Dichlorobenzyl alcohol | 0.07-0.15 |
| Xylitil furfural | 0.05-0.2 |
| Reforcyl | 0.05-0.2 |
| *Triticum vulgare* seed extract | 0.05-0.2 |
| Allantoin | 0.02-0.1 |
| Disodium EDTA dihydrate | 0.02-0.1 |
| *Tamarindus indica* seed polysaccharide | 0.02-0.1 |
| Panthenol | 0.01-0.04 |
| Aperoxid TLA | 0.005-0.02 |
| Sodium hyaluronate | 0.005-0.02 |
| Aqua | as needed to 100 |

Example 6

Antiperspirant Deodorant

| Ingredient | Qty (% w/w) |
|---|---|
| Aluminum chlorohydrate solution 50% | 20-80 |
| Ethyl alcohol | 5-19 |
| Propylheptyl caprylate | 3-13 |
| Glyceryl stearate | 2-6 |
| Polysorbate 60 | 1.1-4.3 |
| Sorbitan stearate | 0.8-3.2 |
| Concentrated *Hamamelis* water | 0.04-0.17 |
| Xylitil furfural | 0.03-0.11 |
| Aqua | as needed to 100 |

Example 7

Cleanser for Acne Skin

| Ingredient | Qty (% w/w) |
|---|---|
| Disodium cocoyl glutamate | 1-4 |
| Decyl glucoside | 3-12 |
| Protelan AG 8 (27%) | 3-11 |
| Sodium methyl cocoyl taurate | 3-11 |
| Oxetal VD 92 | 2-7 |
| Sodium cocoyl glutamate | 0.1-3 |
| Antil 127 | 0.8-3.1 |
| Citric acid | 0.6-2.3 |
| Phenoxyethanol | 0.4-1.0 |
| Parfum | 0.4-1.6 |
| PEG-10 Olive glycerides | 0.3-1 |
| Diazolidinyl Urea | 0.13-0.50 |
| Glycyrrhizinate ammonium | 0.05-0.21 |
| Panthenol | 0.05-0.21 |
| Zinc PCA | 0.05-0.21 |
| Octadecatrienoic acid 50% | 0.01-0.041 |
| Butyl hydroxyanisole (BHA) | 0.005-0.021 |
| Glycyrrhizate dipotassium | 0.005-0.021 |
| Sorbityl benzal | 0.005-0.021 |
| Sodium hydroxide | 0.003-0.011 |
| Aqua | as needed to 100 |

Example 8

Shower-shampoo Detergent

| Ingredient | Qty (% w/w) |
|---|---|
| Sulfetal LA B-E | 8-31 |
| Setacin 103 spezial NP | 6-24 |
| Amphotensid GB 2009 CONC | 3-12 |
| Di-PPG-2 Myreth-10 Adipate | 15-6 |
| Mirustyle MFP PE - LQ - (WD) | 1.2-4.8 |
| Olive oil PEG-7 Esters | 0.9-3.6 |
| Parfum | 0.6-2.4 |
| Sodium hydroxymethylglycinate | 0.5-1.9 |
| Antil 127 | 0.4-1.7 |
| Oxetal VD 92 | 0.4-1.7 |
| Citric acid | 0.3-1.2 |
| Dimethicone PEG-7 Isostearate | 0.3-1.2 |
| Potassium chloride | 0.3-1.2 |
| Polyquaternium-10 | 0.2-1 |
| Panthenol | 0.12-0.48 |
| Tetrasodium EDTA | 0.06-0.24 |
| Butyl hydroxyanisole (BHA) | 0.006-0.024 |
| Sorbityl furfural tetrabenzoate | 0.0012-0.0048 |
| Aqua | as needed to 100 |

Example 9

Soothing After Sun Milk

| Ingredient | Qty (% w/w) |
|---|---|
| Shea butter | 3-10 |
| Mixed decanoyl and octanoyl triglycerides | 3-10 |
| Arlatone 2121 | 2-7 |
| *Calendula* oily extract | 1.5-6.1 |
| Glycerin | 1.5-6.1 |
| Tapioca starch | 1-4 |
| Dimethicone | 0.5-2 |
| Sorbityl benzal | 0.4-1.4 |
| Beta-glycyrrhetic acid 18 | 0.3-1 |
| Phenoxyethanol | 0.3-1 |
| Symdiol 68 | 0.3-1 |
| Lactic acid sol. 80% | 0.2-0.7 |
| Allantoin | 0.15-0.61 |
| Betaine | 0.15-0.61 |
| Inositol | 0.15-0.61 |
| Parfum | 0.15-0.61 |
| Xylitol | 0.15-0.61 |
| Xantan gum | 0.14-0.57 |
| Cetyl hydroxyethylcellulose | 0.13-0.51 |
| Concentrated delta tocopherol | 0.1-0.4 |
| Beta sitosterol | 0.05-0.21 |
| Sodium hydroxide | 0.05-0.21 |
| Disodium EDTA dihydrate | 0.05-0.2 |
| Taurine | 0.05-0.2 |
| Sodium hyaluronate | 0.03-0.1 |
| Aqua | as needed to 100 |

Example 10

First-wrinkle Smoothing Fluid

| Ingredient | Qty (% w/w) |
| --- | --- |
| SFE 839 | 7-30 |
| Polysilicone-11 | 0.5-3 |
| Simulgel 600 | 0.6-2.4 |
| Cyclopentasiloxane | 7.0-31 |
| Polyvinyl alcohol | 0.5-2 |
| Phenoxyethanol | 0.4-1.0 |
| Parfum | 0.3-1.4 |
| Ammonium acryloyldimethyltaurate/VP copolymer | 0.3-1.2 |
| Dimethicone | 0.3-3 |
| Glycerin | 0.2-1 |
| Polysorbate 20 | 0.2-1 |
| Avocadol | 0.2-0.8 |
| Fancol VB | 0.2-0.8 |
| Mannitol | 0.2-0.8 |
| *Moringa Oleifera* seeds extract | 0.2-0.8 |
| Diazolidinyl Urea | 0.12-0.5 |
| *Lactobacillus rhamnosus* T12 | 0.1-0.4 |
| Titanium dioxide silica coated | 0.1-0.4 |
| Natrlquest E 30 | 0.07-0.3 |
| Sorbityl vanillinal | 0.05-0.2 |
| Pullulan | 0.05-0.2 |
| Tocotrienol | 0.01-0.04 |
| Tetrahydrocurcuminoids | 0.005-0.02 |
| Ectoine | 0.002-0.01 |
| Aqua | as needed to 100 |

Example 11

Gels for Scalp with UVA and UVB Protection

| Ingredient | Qty (% w/w) |
| --- | --- |
| Denatured ethyl alcohol, type C | 10-41 |
| Diethylamino Hydroxybenzoyl Hexyl Benzoate | 5-10 |
| Ethylhexyl methoxycinnamate | 4-10 |
| Cyclopentasiloxane | 3-10 |
| Bis-Ethylhexyloxyphenol Methoxyphenyl Triazine | 1.5-6.2 |
| Ethylhexyl triazone | 1.5-5 |
| Zinc oxide | 1.5-6.2 |
| Glycerin | 1-4.1 |
| Octocrylene | 1-4.1 |
| Potassium cetyl phosphate | 1-4.1 |
| Ammonium acryloyldimethyltaurate/VP copolymer | 0.8-3.1 |
| Sepiplus S | 0.8-3.1 |
| Betaine | 0.3-1 |
| Fancol VB | 0.3-1 |
| Sorbityl vanillinal | 0.3-1 |
| Steareth-21 | 0.3-1 |
| Vitamin E acetate | 0.15-0.62 |
| Dehydroxanthan Gum | 0.05-0.19 |
| Lactic acid sol. 80% | 0.03-0.1 |
| Butyl hydroxyanisole (BHA) | 0.03-0.1 |
| Butylatedhydroxytoluene | 0.03-0.1 |
| Disodium EDTA dihydrate | .03-0.1 |
| Sodium hydroxide | 0.03-0.1 |
| Ferulic acid | 0.005-0.021 |
| Catechin | 0.004-0.016 |
| Quercetin | 0.001-0.0041 |
| Aqua | as needed to 100 |

Example 12

Milk with High Sun Protection Filter

| Ingredient | Qty (% w/w) |
| --- | --- |
| Diethylamino Hydroxybenzoyl Hexyl Benzoate | 5-10 |
| Ethylhexyl methoxycinnamate | 5-10 |
| Butylene glycol cocoate | 3-12 |
| C12-15 Alkyl benzoate | 3-12 |
| Dicaprylyl ether | 2-10 |
| Octocrylene | 2-10 |
| Ethylhexyl salicylate | 2-5 |
| Titanium dioxide silica coated | 2-8 |
| PEG-30 Dipolyhydroxystearate | 2-7 |
| Cyclopentasiloxane | 1.5-5.9 |
| Fomblin HC-P2 1000 solution 20% | 1.2-4.7 |
| Butyl methoxydibenzoylmethane | 1-3.9 |
| Glycerin | 0.7-2.9 |
| Glyceryl behenate/eicosadioate | 0.7-2.9 |
| Bentone Gel TNV | 0.5-2 |
| Oxynex ST Liquid | 0.5-2 |
| Magnesium sulphate heptahydrate | 0.4-1.6 |
| Sodium hydroxymethylglycinate | 0.1-0.5 |
| Hydrogenated castor oil | 0.3-1.2 |
| PPG-15 Stearyl ether | 0.2-1 |
| Phenoxyethanol | 0.15-0.59 |
| Citric acid | 0.1-0.39 |
| Parfum | 0.1-0.39 |
| Beta-glycyrrhetic acid 18 | 0.05-0.2 |
| Disodium EDTA dihydrate | 0.02-0.1 |
| Sorbityl vanillinal | 0.02-0.1 |
| Vitamin E acetate | 0.02-0.1 |
| Aqua | as needed to 100 |

Example 13

Specific Protective Cream for Sensitive Skin

| Ingredient | Qty (% w/w) |
| --- | --- |
| PEG-8 Beeswax | 7-26 |
| Mixed decanoyl and octanoyl triglycerides | 5-18 |
| Isooctadecyl isooctadecanoate | 4-16 |
| Uvinul A plus B | 3-11 |
| Denatured ethyl alcohol, type C | 1.5-6 |
| Camomile oil | 1.5-6 |
| Shea butter | 0.8-3 |
| Phytosome glycyrrhetic acid | 0.5-2 |
| Hydroviton | 0.5-2 |
| Sodium hydroxymethylglycinate | 0.1-0.5 |
| Sorbityl furfural tetrabenzoate | 0.4-1.4 |
| Beta-glycyrrhetic acid 18 | 0.3-1 |
| Phenoxyethanol | 0.3-1 |
| Carbomer | 0.2-0.9 |
| Parfum | 0.11-0.44 |
| Alpha bisabolol | 0.1-0.4 |
| Allantoin | 0.1-0.4 |
| Concentrated delta tocopherol | 0.1-0.4 |
| Disodium EDTA dihydrate | 0.08-0.3 |
| Sodium hydroxide | 0.08-0.3 |
| Beta sitosterol | 0.05-0.21 |
| Ascorbyl palmitate | 0.0015-0.006 |
| Aqua | as needed to 100 |

Example 14

"Mineral" High Protection Sunscreen

| Ingredient | Qty (% w/w) |
| --- | --- |
| Zinc oxide (Triethoxycaprylylsilane coated) | 4-20 |
| Titanium dioxide (stearic acid & alumina coated) | 4-20 |
| Caprylic/Capric Triglyceride | 4-20 |
| Dimethicone | 3-10 |
| Dicaprylyl carbonate | 2-7 |
| Glycerin | 1.5-6 |
| Polyoxyethylene (2) stearyl ether | 1.5-6 |

-continued

| Ingredient | Qty (% w/w) |
| --- | --- |
| Cetearyl alcohol | 1-4 |
| Hydrogenated dimer dilinoleyl/dimethylcarbonate copolymer | 1-4 |
| Steareth-21 | 1-4 |
| Polyhydroxystearic acid | 0.5-2.5 |
| Phenoxyethanol | 0.4-1 |
| Xantan gum | 0.3-1 |
| Disodium EDTA dihydrate | 0.06-0.24 |
| Antileukine 6 | 0.05-0.2 |
| O-Cymen-5-OL | 0.05-0.2 |
| Titanium dioxide | 0.05-0.2 |
| Vitamin E acetate | 0.05-0.2 |
| Sorbityl furfural tetraacetate | 0.03-0.1 |
| Ectoine | 0.005-0.02 |
| Aqua | as needed to 100 |

Example 15

Face Scrub

| Ingredient | Qty (% w/w) |
| --- | --- |
| Decyl glucoside | 3-13 |
| Butylene glycol | 2-9 |
| Polyethylene | 2-7 |
| Glycerin | 1.4-5.4 |
| PEG-60 Almond glycerides | 0.7-2.7 |
| Euxyl PE9010 | 0.5-1.1 |
| Poloxamer 188 | 0.5-1.8 |
| Acrylates/C10-30 alkyl acrylate crosspolymer | 0.3-1.3 |
| L-Arginine | 0.3-1.2 |
| Caprylyl glycol | 0.3-1.1 |
| Parfum | 0.2-0.6 |
| Xantan gum | 0.07-0.27 |
| Beta-glycyrrhetic acid 18 | 0.05-0.18 |
| Xylitil furfural | 0.05-0.18 |
| Tetrasodium EDTA | 0.02-0.09 |
| Polyquaternium-10 | 0.02-0.09 |
| Vitamin E acetate | 0.02-0.09 |
| Aqua | as needed to 100 |

Example 16

Medium Protection Sun Milk

| Ingredient | Qty (% w/w) |
| --- | --- |
| Ethylhexyl methoxycinnamate | 5-10 |
| Diethylamino Hydroxybenzoyl Hexyl Benzoate | 3-10 |
| Mixed decanoyl and octanoyl triglycerides | 2-8 |
| Bis-Ethylhexyloxyphenol Methoxyphenyl Triazine | 0.8-3 |
| Fomblin HC-P2 1000 solution 20% | 0.8-3 |
| Panthenol | 0.7-2.7 |
| Bioscontrol synergy BAS | 0.6-1.1 |
| Jojoba oil | 0.5-2 |
| Butyl methoxydibenzoylmethane | 0.3-1 |
| Vitamin E acetate | 0.3-1 |
| PPG-15 Stearyl ether | 0.15-0.61 |
| Acrylates/C10-30 alkyl acrylate crosspolymer | 0.1-0.4 |
| Dermofeel PA-3 | 0.1-0.4 |
| *Calendula* oily extract | 0.1-0.4 |
| Pemulen TR-2 | 0.1-0.4 |
| Parfum | 0.08-0.3 |
| Sodium hydroxide | 0.08-0.3 |
| Xylitil furfural | 0.05-0.2 |
| Acetyl Tyrosine | 0.03-0.1 |
| Carnosine | 0.03-0.1 |
| Beta-glycyrrhetic acid 18 | 0.01-0.04 |
| Aqua | as needed to 100 |

Experimental Studies

The following compounds having general formula (I) according to the invention: xylitil furfural-sorbityl benzal-sorbityl vanillinal-tetracetyl sorbityl furfural-tetrabenzoyl sorbityl furfural, were subjected to the following in vitro activity tests:
MTT assay with induced oxidative stress
Anti-inflammatory TNF-α and LPS activity assay
Skin barrier function protection assay
HORAC Hydroxyl radical antioxidant capacity assay
Biological Models Used
Cultured Human Keratinocytes The immortalized line of human keratinocytes NCTC2544 is used (Perry V. P. et al., 1957), cultured in sterile flasks (25 cm$^3$), incubated at 37° C. in a humid atmosphere at 5% $CO_2$ in RPMI culture medium added with bovine fetal serum (FBS), 2 mm glutamine, 1% non-essential amino acids, in the presence of 1% penicillin and streptomycin. The 1:3 split is done every 2 days upon achieving the monolayer by washing with 1×PBS (phosphate buffer without $Ca^{2+}$ and $Mg^{2+}$) and detachment of cells with a trypsin-EDTA solution at 37° C. for 2 minutes. The cells were kept in culture in 25 cm$^3$ sterile flasks and incubated at 37° C. in a humid atmosphere at 5% $CO_2$.

Controls

MTT Assay with Induced Oxidative Stress

Negative control: untreated cells in RPMI medium added to 2.5% fetal bovine serum (FBS), 1% non-essential amino acids (NEAA), 1% of a penicillin and streptomycin mixture (Pen-Strep Mix), and kept in (96 well) 25 cm$^2$ culture plates at 37° C. and 5% $CO_2$ (in the dark).

Positive control: cells treated for 2 h with 1 mM hydrogen peroxide in RPMI medium added to 2.5% fetal bovine serum (FBS), 1% non-essential amino acids (NEAA), 1% of a penicillin and streptomycin mixture (Pen-Strep Mix), and kept in (96 well) 25 cm$^2$ culture plates at 37° C. and 5% $CO_2$ (in the dark).

Study of the Anti-inflammatory Activity and of the Skin Barrier Function Protection Negative control: untreated cells in RPMI medium added to 2.5% fetal bovine serum (FBS), 1% non-essential amino acids (NEAA), 1% of a penicillin and streptomycin mixture (Pen-Strep Mix), and kept in (12 well) 25 cm$^2$ culture plates at 37° C. and 5% $CO_2$.

Positive control: cells in RPMI medium added to 2.5% fetal bovine serum (FBS), 1% non-essential amino acids (NEAA), 1% of a penicillin and streptomycin mixture (Pen-Strep Mix) and 10 μg/mL LPS (lipopolysaccharide) and kept in (96 well) 25 cm$^2$ culture plates at 37° C. and 5% $CO_2$ (in the dark).

Methods

MTT with Induced Oxidative Stress-NCTC 2544

Principle of the Method:

Studies conducted in 2005 by Rajapakse and collaborators demonstrated the ability to use a highly used and versatile method like that of the MTT assay to study the in vitro antioxidant activity of active compounds. Through this method it is possible to study the protective effects of such compounds on cells then subjected to oxidative stress. The induction of oxidative stress is carried out by incubation with hydrogen peroxide, an agent inducing the production of oxidative damage in cells through the formation of ROS. Any protective effects can be determined through the evaluation of the cell viability post oxidative stress of cells pretreated/pre-exposed to the active compounds to be tested, compared to cells subjected to the same oxidative stress. A greater cell viability will correspond to a protective effect of the compounds tested.

Experimental Procedure:

The assay was conducted in accordance with the method described by Coda and collaborators (Coda et al., 2012), with some changes. Human keratinocytes NCTC2544 were seeded in a 96-well plate at the density of 5*104 cells/well and incubated at 37° C. until reaching about 80% confluence.

Then, the cells were incubated for 16 hours with the active compounds to be tested and the respective controls at the following concentrations: 13.5 µM and 27 µM. The dilutions were prepared starting from 1000× stock in DMSO, sterile-filtered and using RPMI medium added to 2.5% fetal bovine serum (FBS), 1% non-essential amino acids (NEAA), 1% of a penicillin and streptomycin mixture (Pen-Strep Mix). Cells treated with $H_2O_2$ 1 mM were used as a positive control; cells kept in culture medium alone (RPMI 2.5% FCS) were used instead as a negative control. After 16 hours of pre-treatment, the cells were washed with PBS 1× and incubated for 90 minutes with a 1 mm $H_2O_2$ solution (Sigma-Aldrich, St. Louis, Mo., USA) in serum-free medium, in the dark, at 37° C. and 5% $CO_2$.

After the step of induction of the oxidative stress, the cell viability of the samples of the above compounds of the invention was evaluated in accordance with the method described by Mosmann T. Rapid colorimetric assay for cellular growth and survival: application to proliferation and cytotoxicity assays. J Immunol Methods. 1983 Dec. 16; 65(1-2):55-63.

The data were expressed as percentage of cell viability compared with control cells (ctr) not stressed, according to the following formula:

% cell viability/$ctr$=($Abs$ sample/$Abs$ $ctr$)·100

All the assays were performed at least two times in duplicate.

Study of the Anti-inflammatory Activity-NCTC 2544

Experimental Procedure

The gene expression of the TNF-α inflammation marker was evaluated by relative quantitative RT-PCR (quantitative reverse transcription-polymerase chain reaction-qRT-PCR).

This assay involved three sequential steps:
extraction of total RNA;
retrotranscription in cDNA;
qRT-PCR.

Human keratinocytes NCTC 2544 were seeded in 12-well plates at the density of $0.5*10^6_4$ cells/well and incubated until reaching about 80% confluence.

Then, the cells were incubated for 16 and 24 hours with the compounds of the invention to be tested and the respective controls at the following concentrations: 13.5 µM and 27 µM, and admixed (in the well) with 10 µg/ml LPS.

The dilutions were prepared starting from 1000× stock in DMSO, sterile-filtered and using RPMI medium added to 2.5% fetal bovine serum (FBS), 1% non-essential amino acids (NEAA), 1% of a penicillin and streptomycin mixture (Pen-Strep Mix).

Cells kept in the culture medium alone (RPMI 2.5% FBS) were used as a negative control.

Cells in the culture medium alone (RPMI 2.5% FBS) and treated only with 10 µg/mL LPS were used as a positive control.

After incubation, the RNA was extracted. Total RNA was extracted from NCTC 2544 cells using the commercial kit Ribospin™ (GeneAllBiotechnology Co., LTD).

At the end of incubation with the active compounds of the invention, cells were washed with PBS (1×) and finally subjected to RNA extraction procedure. At the end of the extraction, using a spectrophotometer (Jenway UV/VIS MOD: 6715, BS-6715B0), concentrations were calculated in µg/mL of total RNA extracted at a wavelength of 260 nm.

Finally, the integrity of RNA (2 µg/mL) was assessed by means of an electrophoresis run on 1% agarose gel.

The total RNA was converted into cDNA (complementary DNA), using an enzyme capable of synthesizing a DNA molecule using a strand of RNA as a template; this DNA-polymerase RNA-dependent enzyme is called reverse transcriptase.

It binds to the 3' end of a single strand of RNA and using random primers and deoxynucleoside triphosphate (DNTPS) synthezises the strand of cDNA.

To this end, a commercial kit "PrimeScript™ RT Reagent Kit (perfect Real Time)" (TakaraBioInc., Japan) was used, containing 5× PrimeScript Buffer (for real Time); PrimeScript RT Enzyme Mix1; OligodTPrimer; Random 6 mers; RNAse free dH2O. The extracted and quantified RNA was diluted to a concentration of 2 µg/mL and reverse transcribed into cDNA. A Master Mix of 10 µL (containing 5× PrimeScript Buffer (for real Time); PrimeScript RT Enzyme Mix1; OligodTPrimer 50 µM; Random 6 mers 100 µM) was prepared, to which 10 µL of RNA (2 µg/mL) were added.

The samples were placed in a thermal cycler (Stratagene Mx3000P Real Time PCR System, Agilent Technologies Italy S.p.A., Milan, Italy) and subjected to retrotranscription under the following conditions:
37° C. for 15 minutes;
85° C. for 5 seconds;
4° C. hold.

At the end of the retrotranscription, samples were added 30 µL of DEPC water to obtain a final concentration of cDNA of 40 ng/µL.

The qRT-PCR is a real-time amplification and quantification method of amplified products by monitoring the fluorescence emitted during the reaction.

For RT-PCR amplification, the TaqMan® probe (Applied-Biosystems) method was used. The following TYaqMan probe was used: Hs00174128_m1 (TNF-α). GAPDH: Hs99999905_m1 was used as control gene (housekeeping).

The Taqman probe is a type of probe which allows the development of fluorescence as the amplification advances. A reporter (fluorophore FAMTM) is bound to its 5' end while a quencher is bound to the 3' end. The closeness between the reporter and the quencher cancels the fluorescence signal emission. Only with the 5' esonucleasic activity 5' of thermostable DNA polymerase (Taq polymerase) fluorescence is detected and the accumulation of the amplification products can be evaluated through the increase of fluorescence of the reporter which increases with each cycle.

A Master Mix was set up for the qRT-PCR as follows:
10 µL of "2× Premix Ex Taq";
1 µL of "20× TaqMan Gene ExpressionAssays" (containing 2 primers and the fluorophore-labeled fluorescent probe FAMTM);
0.4 µL of passive reference Rox II;
5 µL of DEPC water.

4 µL of cDNA were added to the Master Mix for the target gene and 1 µL of cDNA for the housekeeping gene.

The amplification was carried out for 40 runs under the following conditions:
95° C., 30 sec (Amplitaqactivation);
95° C., 5 sec (Denaturation)
60° C., 20 sec (Annealing-extension);

Each assay was conducted in duplicate.

The data obtained were analyzed according to the method of 2-ΔΔCt and so it was possible to calculate the relative values of expression of the gene of interest, normalized compared to the housekeeping gene and calibrated on the control sample (untreated cells):

$$\Delta Ct = \Delta Ct_{target-housekeeping} \text{ (control)} - \Delta Ct_{target-housekeeping} \text{ (treated cells)}$$

The $2^{-\Delta\Delta Ct}$ was calculated assuming an amplification efficiency of 100%.

Study of the Skin Barrier Function Protection

Experimental Procedure

The gene expression of the involucrin (IVL) and fillagrin (FLG) markers was evaluated by relative quantitative RT-PCR (quantitative reverse transcription-polymerase chain reaction-qRT-PCR).

This assay involved three sequential steps:
extraction of total RNA;
retrotranscription in cDNA;
qRT-PCR.

Human keratinocytes NCTC2544 were seeded in 12-well plates at the density of $0.5*10^6$ cells/well and incubated until reaching about 80% confluence.

Then, the cells were incubated for 16 and 24 hours with the active compounds to be tested and the respective controls at the following concentrations: 13.5 and 27 µM, and admixed (in the well) with 10 µg/ml LPS.

The dilutions were prepared starting from 1000× stock in DMSO, sterile-filtered and using RPMI medium added to 2.5% fetal bovine serum (FBS), 1% non-essential amino acids (NEAA), 1% of a penicillin and streptomycin mixture (Pen-Strep Mix).

Cells kept in the culture medium alone (RPMI 2.5% FBS) were used as a negative control.

Cells in the culture medium alone (RPMI 2.5% FBS) and treated only with 10 µg/mL LPS were used as a positive control.

After incubation, the RNA was extracted. Total RNA was extracted from NCTC 2544 cells using the commercial kit Ribospin™ (GeneAllBiotechnology Co., LTD).

At the end of incubation with the active compounds of interest, cells were washed with PBS (1×) and finally subjected to RNA extraction procedure. At the end of the extraction, using a spectrophotometer (Jenway UV/VIS MOD: 6715, BS-6715B0), concentrations were calculated in µg/mL of total RNA extracted at a wavelength of 260 nm.

Finally, the integrity of RNA (2 µg/mL) was assessed by means of an electrophoresis run on 1% agarose gel.

Total RNA was converted into cDNA (complementary DNA), using an enzyme capable of synthesizing a DNA molecule using a strand of RNA as a template; this DNA-polymerase RNA-dependent enzyme is called reverse transcriptase.

It binds to the 3' end of a single strand of RNA and using random primers and deoxynucleoside triphosphate (DNTPS) synthezises the strand of cDNA.

To this end, a commercial kit "PrimeScript™ RT Reagent Kit (perfect Real Time)" (TakaraBioInc., Japan) was used, containing 5× PrimeScript Buffer (for real Time); PrimeScript RT Enzyme Mix1; OligodTPrimer; Random 6 mers; RNAse free dH2O.

The extracted and quantified RNA was diluted to a concentration of 2 µg/mL and reverse transcribed into cDNA. A Master Mix of 10 µL (containing 5× PrimeScript Buffer (for real Time); PrimeScript RT Enzyme Mix1; OligodTPrimer 50 µM; Random 6 mers 100 µM) was prepared, to which 10 µL of RNA (2 µg/mL) were added.

The samples were placed in a thermal cycler (Stratagene Mx3000P Real Time PCR System, Agilent Technologies Italy S.p.A., Milan, Italy) and subjected to retrotranscription under the following conditions:
37° C. for 15 minutes;
85° C. for 5 seconds;
4° C. hold.

At the end of the retrotranscription, samples were added 30 µL of DEPC water to obtain a final concentration of cDNA of 40 ng/µL.

The qRT-PCR is a real-time amplification and quantification method of amplified products by monitoring the fluorescence emitted during the reaction.

For RT-PCR amplification, the TaqMan® probe (AppliedBiosystems) method was used. The following TYaqMan probe was used: Hs00846307_s1 (IVL) and Hs00863478_g1 (FLG).

GAPDH: Hs99999905_m1 was used as control gene (housekeeping).

The Taqman probe is a type of probe which allows the development of fluorescence as the amplification advances. A reporter (fluorophore FAMTM) is bound to its 5' end while a quencher is bound to the 3' end. The closeness between the reporter and the quencher cancels the fluorescence signal emission. Only with the 5' esonucleasic activity 5' of thermostable DNA polymerase (Taq polymerase) fluorescence is detected and the accumulation of the amplification products can be evaluated through the increase of fluorescence of the reporter which increases with each cycle.

A Master Mix was set up for the qRT-PCR as follows:
10 µL of "2× Premix Ex Taq";
1 µL of "20× TaqMan Gene ExpressionAssays" (containing 2 primers and the fluorophore-labeled fluorescent probe FAMTM);
0.4 µL of passive reference Rox II;
5 µL of DEPC water.
4 µL of cDNA were added to the Master Mix for the target gene and 1 µL of cDNA for the housekeeping gene.

The amplification was carried out for 40 runs under the following conditions:
95° C., 30 sec (Amplitaqactivation);
95° C., 5 sec (Denaturation);
60° C., 20 sec (Annealing-extension);
Each assay was conducted in duplicate.

The data obtained were analyzed according to the method of 2-ΔΔCt and so it was possible to calculate the relative values of expression of the gene of interest, normalized compared to the housekeeping gene and calibrated on the control sample (untreated cells):

$$\Delta\Delta Ct = \Delta Ct_{target-housekeeping} \text{ (control)} - \Delta Ct_{target-housekeeping} \text{ (treated cells)}$$

The $2^{-\Delta\Delta Ct}$ was calculated assuming an amplification efficiency of 100%.

HORAC Assay: Hydroxyl Antioxidant Capacity In Vitro

Experimental Procedure

The commercial kit "Oxiselect Hydroxyl Radical Antioxidant Capacity (HORAC) activity assay" (Cell Biolabs).

The HORAC assay esxpresses the compound antiradical capacity towards the hydroxyl radical OH' and is based on the oxidation of a fluorescent probe by hydroxyl radicals through a hydrogen transfer process (HAT). Hydroxyl radicals are produced by a radical initiator hydroxyl and by Fenton's reagent, which quenches the fluorescent probe over time. The antioxidants present in the sample block the oxidation by the hydroxyl radical of the fluorescent probe until the antioxidant activity in the sample runs out. The remaining hydroxyl radicals destroy the fluorescence of the fluorescent probe. The antioxidant capacity of the sample is related to the fluorescence decay curve, which usually is represented as the area under the curve (AUC). The AUC is used to quantify the total antioxidant activity of the hydroxyl radical in a sample and is compared to the curve of an antioxidant standard.

The compounds of the invention were tested at the following concentrations: 13.5 µM; 27 µM, 13.5 mM; 27 mM.

For comparison purposes, also samples of the compound monofurfurylidene-2.4-sorbitol defined below by the acronym ARGB11, were in this case tested under the same two concentrations, as a reference compound according to EP0345362 mentioned above as the background art of substances with free radical inhibition activity.

Results

Cell Protection from Induced Oxidative Stress

The percentage of protection of various compounds of the invention at the two concentrations tested is as follows:

|  | % protection | |
|---|---|---|
|  | 13.5 µM | 27 µM |
| Tetracetyl sorbityl furfural | 34.385 | 49.201 |
| Tetrabenzoyl sorbityl furfural | 36.035 | 8.725 |
| Sorbityl benzal | 11.673 | 20.439 |
| Sorbityl vanillinal | 11.320 | 22.766 |
| Xylitil furfural | 59.554 | 33.651 |

It is generally noted that all the tested compounds of the invention have an activity of protection of cells from the induced oxidative stress. In particular, the protection values obtained at the lower dose for xylitil furfural and at the higher dose for tetracetyl sorbityl furfural appear remarkable.

Anti-inflammatory Activity

The data obtained for the various compounds of the invention at the two concentrations tested is as follows:

|  | TNF-α Comparison vs LFS (%) | | | |
|---|---|---|---|---|
|  | 16 h | 24 h | 16 h | 24 h |
| Control | 1.00 | 1.00 | — | — |
| Control + LPS | 3.20 | 20.36 | — | — |
| Tetracetyl sorbityl furfural 13.5 µM | 0.35 | 5.75 | 89.06 | 71.78 |
| Tetracetyl sorbityl furfural 27 µM | 0.28 | 0.12 | 91.18 | 99.39 |
| Tetrabenzoyl sorbityl furfural 13.5 µM | 0.63 | 2.51 | 80.28 | 87.69 |
| Tetrabenzoyl sorbityl furfural 27 µM | 0.45 | 0.28 | 85.81 | 98.63 |
| Sorbityl benzal 13.5 µM | 0.39 | 0.71 | 87.93 | 96.50 |
| Sorbityl benzal 27 µM | 0.08 | 0.01 | 97.62 | 99.97 |
| Sorbityl vanillinal 13.5 µM | 0.04 | 0.09 | 98.64 | 99.57 |
| Sorbityl vanillinal 27 µM | 0.15 | 0.21 | 95.44 | 98.95 |
| Xylitil furfural 13.5 µM | 0.03 | 0.03 | 98.96 | 99.85 |
| Xylitil furfural 27 µM | 0.18 | 0.18 | 94.37 | 99.10 |

The values obtained show that all the compounds of the invention have anti-inflammatory activity, at various test concentrations and times.

In particular, the values for sorbityl vanillinal and xylitil furfural at the lower dose are remarkable, while at the higher dose, sorbityl benzal appears particularly significant.

Effect on the Skin Barrier

The data obtained in this regard are as follows:

|  | (IVL) 16 h RQ ± SEM | (FLG) 16 h RQ ± SEM |
|---|---|---|
| Control + LPS | 1.000 ± 0.284 | 1.000 ± 0.195 |
| Tetracetyl sorbityl furfural 13.5 µM | 57.282 ± 17.060 | 11.158 ± 5.679 |
| Tetrabenzoyl sorbityl furfural 13.5 µM | 9.563 ± 1.159 | 22.864 ± 7.892 |
| Sorbityl benzal 13.5 µM | 6.646 ± 1.733 | 16.971 ± 2.987 |
| Sorbityl vanillinal 13.5 µM | 18.347 ± 1.664 | 4.408 ± 2.683 |
| Xylitil furfural 13.5 µM | 60.653 ± 14.549 | 64.669 ± 6.930 |

They show that all the tested compounds of the invention greatly stimulate involucrin (IVL) and filaggrin (FLG), are thus able to carry out a recovery action of the skin barrier function in the event of alterations therein, for example due to inflammation, thus supporting the integrity thereof.

HORAC Test: Antioxidant Hydroxyl Capacity In Vitro

The data obtained with reference to the four different dosages, i.e. 13.5 µM; 27 µM; 13.5 mM; 27 mM, of each tested compound the invention are collected in the following table:

|  | HORAC (Hydroxyl Radical Antioxidant Capacity) µMole GAE/L | | | |
|---|---|---|---|---|
|  | 13.5 µM | 27 µM | 13.5 mM | 27 mM |
| ARGB11 (reference) | 31.04 | 40.110 | 308.497 | 408.795 |
| Tetraacetyl sorbitylfurfural | 797.50 | 171.083 | 330.960 | 428.775 |
| Tetrabenzoyl sorbitylfurfural | 37.65 | 41.485 | 300.856 | 211.479 |
| Sorbityl benzal | 31.04 | 40.110 | 308.497 | 408.795 |
| Sorbityl vanillinal | 70.29 | 115.422 | 3544.098 | 3261.945 |
| Xylitil furfural | 418.69 | 524.692 | 897.479 | 1242.582 |

The HORAC test showed that all the compounds of the invention have an antioxidant effect (expressed as µMole gallic acid equivalent/L).

In particular, at the lower concentrations 13.5 µM and 27 µM, the sorbityl vanillinal, tetraacetyl sorbityl furfural and xylitil furfural compounds according to the invention have an activity—even markedly—higher than the selected reference ARGB11, while tetrabenzoyl sorbityl furfural and sorbityl benzal still have a fully comparable activity.

At the higher dosages, (13.5 µM and 27 µM), the sorbityl vanillinal and xylitil furfural compounds according to the invention have a higher activity than the selected reference ARGB11, while tetraacetyl sorbitylfurfural, tetrabenzoyl sorbityl furfural and sorbityl benzal still have a fully comparable activity.

Therefore, all the experimental data show that all the compounds of formula (I) according to the invention subjected to the tests described have a strong inhibitory activity of free radicals, in addition combined with surprising combined anti-inflammatory effects, skin barrier function protection and inhibition of the induced oxidative stress which make them suitable for an effective and large pharmaceutical use in dermatology for broader clinical conditions, such as from sensitive skin to atopic dermatitis, or in cosmetics for the well-being and health of the human skin, including the scalp, particularly in order to prevent premature aging thereof.

The invention claimed is:

1. A compound selected from:

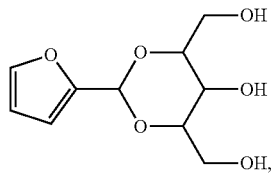

xylitilfurfural

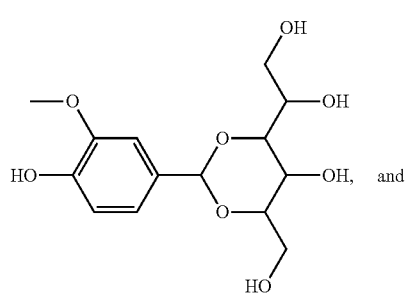

sorbitylvanillinal

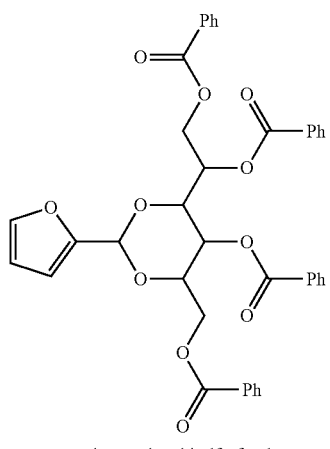

tetrabenzoyl sorbitylfurfural for pharmaceutical use as an active principle in the dermatological field when topically administered on skin or scalp to preserve or restore the barrier function of the involved cutis together with an anti-inflammatory activity and an antioxidant activity against free radicals.

2. A pharmaceutical composition for topical administration on skin or scalp to preserve or restore the barrier function of the involved cutis together with an anti-inflammatory activity and an antioxidant activity against free radicals, comprising as an active principle selected from:

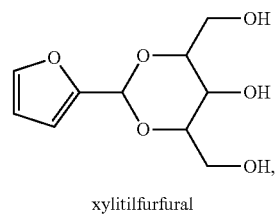

xylitilfurfural

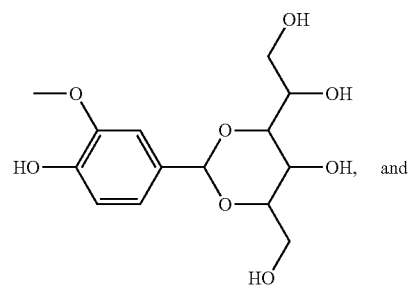

sorbitylvanillinal

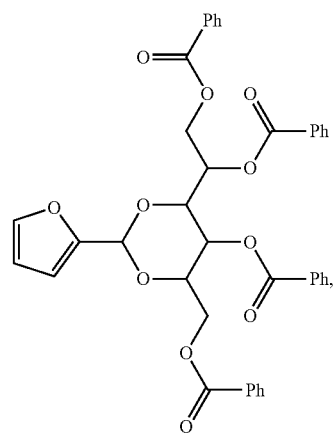

tetrabenzoyl sorbitylfurfural formulated together with components for topical administration on the skin or scalp.

3. A cosmetic composition for topical administration on skin or scalp to preserve or restore the barrier function of the involved cutis together with an anti-inflammatory activity and an antioxidant activity against free radicals, comprising as an active principle a compound selected from:

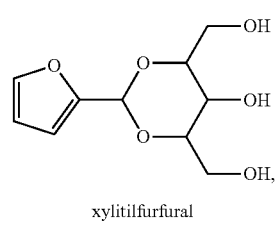

xylitilfurfural

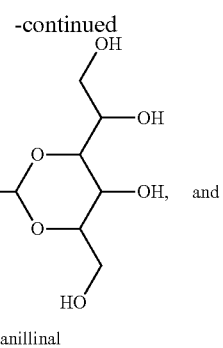

sorbitylvanillinal

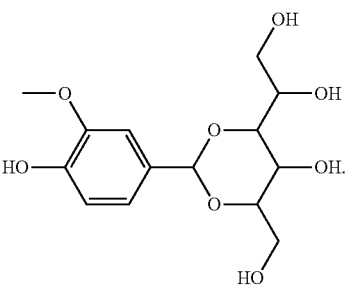 [SMILES: COc1cc(C2OC(CO)C(O)C(C(O)CO)O2)ccc1O]

tetrabenzoyl sorbitylfurfural formulated together with components for topical administration on the skin or scalp.

4. The composition according to claim 2 comprising said active principle in an amount ranging from 0.001 to 2.0% w/w based on the weight of the composition.

5. Compound of formula (I) characterized in that it is sorbitylvanillinal:

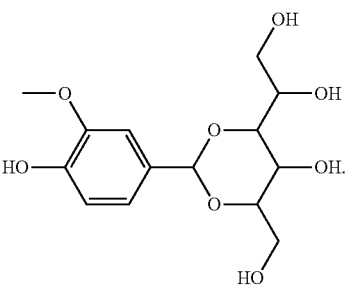 [SMILES: COc1cc(C2OC(CO)C(O)C(C(O)CO)O2)ccc1O]

6. The composition according to claim 3 comprising said active principle in an amount ranging from 0.001 to 2.0% w/w based on the weight of the composition.

* * * * *